US006355449B1

(12) United States Patent
Chen et al.

(10) Patent No.: US 6,355,449 B1
(45) Date of Patent: Mar. 12, 2002

(54) METHOD AND MEDIUM FOR DETECTING VANCOMYCIN-RESISTANT ENTEROCOCCUS

(75) Inventors: Chung-Ming Chen, Falmouth, ME (US); Stephen C. Edberg, Orange, CT (US)

(73) Assignee: Idexx Laboratories, Inc., Westbrook, ME (US)

( * ) Notice: Subject to any disclaimer, the term of this patent is extended or adjusted under 35 U.S.C. 154(b) by 0 days.

(21) Appl. No.: 09/597,951

(22) Filed: Jun. 20, 2000

Related U.S. Application Data

(63) Continuation of application No. 08/690,196, filed on Jul. 26, 1996, now abandoned.

(51) Int. Cl.[7] .............................. C12Q 1/20; C12Q 1/14; C12Q 1/10; C12P 33/10; G01N 33/571

(52) U.S. Cl. .............................. 435/34; 435/38; 435/61; 435/7.36; 435/39; 435/29; 435/16; 435/7.2; 435/885; 435/36

(58) Field of Search .............................. 435/41, 34, 38, 435/7.34, 39, 29, 14, 7.2, 885

(56) References Cited

U.S. PATENT DOCUMENTS

| | | | |
|---|---|---|---|
| 3,206,317 A | 9/1965 | Golber | 99/192 |
| 3,496,066 A | 2/1970 | Berger et al. | 195/103.5 |
| 4,235,964 A | 11/1980 | Bochner | 435/34 |
| 4,259,442 A | 3/1981 | Gayral | 435/36 |
| 4,591,554 A | 5/1986 | Koumura et al. | 435/18 |
| 4,925,789 A | 5/1990 | Edberg | 435/38 |
| 5,164,301 A | 11/1992 | Thompson et al. | 435/29 |
| 5,464,755 A | 11/1995 | Bochner | 435/34 |
| 5,541,082 A * | 7/1996 | Botcher | 435/34 |
| 5,620,865 A * | 4/1997 | Chen et al. | 435/34 |

FOREIGN PATENT DOCUMENTS

| | | |
|---|---|---|
| EP | 0261 934 | 9/1987 |
| EP | 0 254 771 B1 | 12/1992 |
| FR | 78-02436 | 1/1978 |
| WO | WO 94/08043 | 4/1994 |
| WO | 95 04157 A | 2/1995 |
| WO | WO 95/04157 | 2/1995 |
| WO | 96 15435 A | 5/1996 |
| WO | WO 96/15435 | 5/1996 |

OTHER PUBLICATIONS

Dascal et al.; PYR–Positive aerococcus spp.. Clin. Microbio. Newsletter; 12 (5); pp. 38–39, 1990.*
Bacteriological Ambient Water Quality Criteria for Marine and Fresh Recreational Waters; Ambient Water Quality Criteria for Bacteria; USEPA; (1986).
Bergey's Manual of Systematic Bacteriology; Williams and Wilkins; vol. 2; pp. 999–1103; (1989).
Bosley, G. S. et al.; Rapid Identification of Enterococci; Journal of Clinical Microbiology; vol. 18, No. 5; pp. 1275–1277; (Nov., 1983).
Cabelli, V. J. et al.; A marine recreational water quality criterion consistent with indicator concepts and risk analysis; Journal WPCF; vol. 55, No. 10; pp. 1306–1314 (1983).
Cabelli, V. J.; Swimming–Associated Illness and Recreational Water Quality Criteria; Wat. Sci. Tech.; vol. 21, No. 2; pp. 13–21; (1989).
Damaré, et al.; Simplified Direct Plating Method for Enhanced Recovery of Escherichia coli in Food; Journal of Food Science; vol. 50; pp. 1735,1737 and 1746; (Nov.–Dec. 1985).
Dascal, et al.; PYR–Positive Aerococcus spp.; Clinical Microbiology Newsletter, vol. 12; No. 5, pp. 38–39; (Mar. 1, 1990).
de Man, J.C.; The Probability of Most Probable Numbers; European J.Appl.Microbiol.; No. 1, 67–78; (1975).
Donnelly, L. Scott et al.; Gentamicin–Based Medium for the Isolation of Group D Streptococci and Application of the Medium to Water Analysis; Applied and Environmental Microbiology; pp. 576–581; (Mar., 1978).
Edmond, et al.; Vancomycin–Resistant Enterococcus faecium Bacteremia: Risk Factors for Infection; Clinical Infectious Diseases; vol. 20; pp. 1126–1133; (May, 1995).
Emori, T. Grace, et al.; An Overview of Nosocomial Infections, Including the Role of the Microbiology Laboratory; Clinical Microbiology Reviews; vol. 6, No. 4; pp. 428–442 (1993).
Enzymes; 3rd edition, edited by Malcolm Dixson, Edwin C. Webb, C.J.R. Thorne, and K.F. Tipton, Academic Press, U.S.A.; pp. 612–613; (1979).
Fecal Streptococcus and Enterococcus Groups; Standard Methods for the Examination of Water and Wastewater; 18th Edition; pp. 9–69 through 9–73; (1992).
Gatti, M., et al.; A new simple medium for the detection of Enterococcus faecalis and Enterococcus faecium by measurement of conductance changes; Letters in Applied Microbiology; vol. 17, pp. 72–74; (1993).

(List continued on next page.)

Primary Examiner—Ali R. Salimi
Assistant Examiner—Bao Qun Li
(74) Attorney, Agent, or Firm—Howrey Simon Arnold & White, LLP

(57) ABSTRACT

A microbe-specific medium for detection of vancomycin-resistant Enterococci in a test sample within 24 hours and preferably within 18 hours. The testing medium provides a selective growth medium for vancomycin-resistant Enterococci and includes specific nutrient indicators which only the target microbe can significantly metabolize and use for growth. The nutrient indicator contain a nutrient moiety and a detectable moiety linked together by a covalent bond. The nutrient indicators produce detectable signals only if the nutrient indicators are hydrolyzed by the Enterococci specific enzymes including β-glucosidase and pyrrolidonyl arylamidase.

13 Claims, No Drawings

OTHER PUBLICATIONS

Green et al.; *Recovery of Vancomycin–Resistant GramPositive Cocci from Children*; Journal of Clinical Microbiology; pp. 484–488; (Mar., 1990).

Hernandez, et al.; *MPN Miniaturized Procedure for the Enumeration of Faecal Enterococci in Fresh and Marine Waters: The Must Procedure*; Wat. Res.; vol. 27, No. 4; pp. 597–606 (1993).

Kilian, M. et al; *Rapid Identification of Enterobacteriaceae*; Acta path. Microbiol. Scand.; Sect. B 87: pp. 271–276; (1979).

Knudtson, L. M., et al., *Comparison of Fluorescent Gentamicin–Thallous–Carbonate and KF Streptococcal Agars To Enumerate Enterococci and Fecal Streptococci in Meats*; Applied and Environmental Microbiology; pp. 936–938; (Mar. 1993).

Lachica, R.V.F., et al.; *Two Improved Meida for Isolating and Enumerating Enterococci in Certain Frozen Foods*; J. appl. Bact.; No. 31; pp. 151–156; (1968).

Landman, D., et al.; *Comparison of Five Selective Media for Identifying Fecal Carriage of Vancomycin–Resistant Enterococci*; Journal of Clinical Microbiology; pp. 751–752; (Mar., 1996).

Littel, K. J. et al; *Fluorogenic Selective and Differential Medium for Isolation of Fecal Streptococci†*; Applied and Environmental Microbiology; vol. 45, No. 2; pp. 622–627; (Feb., 1983).

Manafi, M., et al.; *Rapid Identification of Enterococci with a New Fluorogenic–Chromogenic Assay*; Water Science and Technology; vol. 27; No. 3–4; pp. 271–274; (1993).

Martin, et al.; *Intérêt des millieux contenant des substrats chromogenes pour l'identification et la numeration des bacteries urinaires*; Pathologie Biologie ; 43(9): 749–753; (1995).

Mooney et al.; *Testing the Waters, A National Perspective on Beach Closings*; Natural Resources Defense Council, pp. 1–67, (Jul. 1992).

Morris, *VRE: Are We Losing the Battle?*; Infectious Disease Alert; 14:189–190 (1995).

*Multiple–Tube Fermentation Technique for Members of the Coliform Group*; Standard Methods for the Examination of Water and Wastewater; 18$^{th}$ Ed.; pp. 9–45—9–64; (1992).

Murray; *The Life and Times of the Enterococcus*; Clinical Microbiology Reviews; pp. 46–65; (Jan., 1990).

Panosian, K. J., et al.; *Rapid Identification of Streptococcus bovis by Using Combination Constitutive Enzyme Substrate Hydrolyses*; Journal of Clinical Microbiology; vol. 27, No. 8; pp. 1719–1722; (Aug., 1989).

Peeler, et al.; *The Most Probable Number Technique*; Compendium of Methods for the Microbiological Examination of Foods; American Public Health Association; Chapter 6, pp. 105–120; Chapter 16, pp. 239–249; (1992).

*Preventing the Spread of Vancomycin Resistance—Report From the Hospital Infection Control Practices Advisory Committee; Comment Period and Public Meetings; Notice*; Department of Health and Human Services, Federal Register, vol. 59, No. 94, pp. 25758–25763 (May 17, 1994).

*Recommendations for Preventing the Spread of Vancomycin Resistance*; Infection Control Hospital Epidemiology; vol. 16, No. 2, pp. 105–113; (Feb., 1995).

*Recommendations for Preventing the Spread of Vancomycin Resistance*; Morbidity and Mortality Weekly Report, U.S. Department of Health and Human Services; vol. 44/No. RR–12; (Sep. 22, 1995).

Thomas, Jr., H.A; *Bacterial Densities From Fermentation Tube Tests*; Journal of the American Water Works Association; vol. 34, No. 4; pp. 572–576; (1942).

Trepeta, R., et al.; *Esculinase (β–glucosidase) for the rapid estimation of activity in bacteria utilizing a hydrolyzable substrate, p–nitrophenyl–β–D–glucopyranoside*; Antonie van Leeuwenhoek, Journal of Microbiology; No. 53; pp. 273–277; (1987).

Bosley et. al., "Rapid Identification of Enterococci," *J. Clin. Microbiol.* 18:1275–1277 (1983).

Damare et al., "Simplified Direct Plating Method for Enhanced Recovery of *Escherichia coli* on Food," *J. Food Science* 50:1736–1738 (1985).

Department of Health and Human Services, CDC, "Preventing the Spread of Vancomycin Resistance—a Report from the Hospital Infection Control Practices Advisory Committee Prepared by the Subcommittee on Prevention and Control of Antimicrobial–Resistant Microorganisms in Hospitals; Comment Period and Public Meeting," *Federal Register* 59:25758–24673 (1994).

Edmond et al., "Vancomycin–Resistant *Enterococcus faecium* Bacteremia: Risk Factors for Infection," *Clin. Inf. Dis.* 20:1126–1133 (1995).

Emori and Gaynes, "An Overview of Nosocomial Infections, Including the Role of the Microbiology Laboratory," *Clin. Microbiol. Rev.* 6:428–442 (1993).

Hospital Infection Control Practices Advisory Committee, "Recommendations for Preventing the Spread of Vancomycin Resistance," *Infection Control Hospital Epidemiology* 16:105–113 (1995).

Kilian and Bulow, "Rapid Identification of Enterobacteriaceae," *Acta Path. Microbiol. Scand. Section B* 87:271–276 (1979).

Lachica et al., "Two Improved Media for Isolating and Enumerating Enterococci in Certain Frozen Foods," *J. Appl. Bacteriol.* 31:151–156 (1968).

Landman et al., Comparison of Five Selective Media for Identifyig Fecal Carriage of Vancomycin–Resistant Enterococci *J. Clin. Microbiol.* 34:751–752 (1996).

Littel and Hartman, "Fluorogenic Selective and Differential Medium for Isolation of Fecal Streptococci," *Applied and Environmental Microbiology* 45:622–627 (1983).

Morris, "VRE: Are We Losing the Battle?" *Infectious Disease Alert*. 14:189–190 (1995).

Murray, "The Life and Times of the Enterococcus," *Clin. Microbiol. Rev.* 3(1):46–65 (1990).

U.S. Department of Health and Human Services—Public Health Service, "Recommendations for Preventing the Spread of Vancomycin Resistance—Recommendations of the Hospital Infection Control Practices Advisory Committee (HICPAC)," *MMWR Reccomendations and Reports* vol. 44/No. RR–12 (Sep. 22, 1995).

Landman, et al., "Comparison of Five Selective Media for Identifying Fecal Carriage of Vancomycin–Resistant Enterococci" *J. Clin. Microbiology* 34(3):751–752 (1996).

Dascal, et al, "PYR–Positive Aerococcus Spp." Clinical Microbiology Newsletter vol. 12(5): 38–39, 1990.

Morris, et al, "Rapid Identification of enterococci with . . . " Water Science Tech. 27(3–4), 1992.

Green,et al, "Recovery of Vancomycin–resistant gram–positive . . . " J. Clin. Micro. 28(3):484–488, 1990.

\* cited by examiner

METHOD AND MEDIUM FOR DETECTING VANCOMYCIN-RESISTANT ENTEROCOCCUS

This application is a continuation of U.S. Ser. No. 08/690,196, filed Jul. 6, 1996, now abandoned, which is hereby incorporated by reference in its entirety.

FIELD OF THE INVENTION

This invention is in the field of chemistry, biology and microbiology and relates to methods and compositions for detecting the presence of vancomycin-resistant Enterococci in a sample of a possibly contaminated material.

BACKGROUND OF THE INVENTION

Enterococci are gram-positive bacteria that inhabit the gastrointestinal tract of healthy individuals. These bacteria have been identified as opportunistic pathogens for humans. Diseases caused by Enterococci include endocarditis, enterococcal bacteremia, urinary tract infections, neonatal infections, central nervous system infections (rare), intraabdominal and pelvic infections. Enterococci have emerged as one of the leading causes of nosocomial infections, responsible for 10% of all infections acquired in the hospital (Emori, T. G. and Gaynes, R. P. *Clin. Microbiol. Rev.* 6:428–42, 1993).

Recent alert about Enterococci is caused not only by their increasing role in nosocomial infections, but also by their resistance to vancomycin, an antibiotic that has been used for treating infection caused by gram positive cocci. Vancomycin resistant Enterococci, emerged as the nosocomial pathogen of the 1990s, have only been discovered in the late 1980s. From 1989 through 1993, the percentage of nosocomial infections reported by the United States Center for Disease Control's National Nosocomial Infections Surveillance system that were caused by vancomycin-resistant Enterococci increased from 0.3% to 7.9% (CDC, MMWR Report 1995). Vancomycin resistant Enterococci have raised the public's anxieties and prompt intense infection control measures in hospitals around the world because no known effective therapy exists for life-threatening vancomycin-resistant enterococcal infections.

Statistics based on the United States Center for Disease Control indicated that 10% of the enterococcal infections are caused by vancomycin-resistant Enterococci with an approximate 60% of mortality rate. The World Health Organization acknowledged that vancomycin-resistant Enterococci are one of the most serious threats to human health. Recommendations for preventing the spread of vancomycin resistance have been extensively discussed in *Infectious Disease Alert* vol. 14, 185, 189, 1995; 44 *MMWR*, RR-12, 1995; Edmond et al., *Clin. Inf. Dis.* 20:1126, 1995; 59 Federal Register 25758, 1994; and 16 *Infection Control Hospital Epidemiology*, 105, 1995.

Prompt detection and reporting of vancomycin-resistant Enterococci isolates are critical for preventing endemic spread of vancomycin-resistance Enterococci and allowing proper treatment once the right drug becomes available.

Currently, numerous vancomycin-containing selective media are used in the surveillance of vancomycin-resistant Enterococci. There is, however not a commercially available method which allows accurate, easy, and rapid detection of this important nosocomial pathogen. Recently, Landman et al.,*J. Clin. Microbiol.* (1996) 34:751–752, described the use of five selective media or identifying fecal carriage of vancomycin-resistant Enterococci.

A common procedure for detecting vancomycin resistant Enterococci by all these available methods involves adding a suspect specimen into a sterile culture medium containing all the necessary elements for bacterial growth. The media may be a liquid medium or a solid agar medium. The sample may be natural or pretreated, as by transporting the sample in a preservative medium before adding it to the selective culture medium and the medium often contain vancomycin to selective for vancomycin-resistant Enterococci. Usually, these culture media are sterilized to prevent interference from contaminating microbes, and an incubation period of from 48 to 72 hours are required for detection of vancomycin-resistant Enterococci.

One major problem for using these types of selective media is that many bacteria are intriscally resistant to vancomycin. Examples include almost of the gram negative bacteria and some gram positive bacteria (Lactobacillus spp. Pediococcus spp., and Leuconostoc spp.). Once growth is observed in these culture media, the target microbes must be isolated and confirmed through selective isolation and one or more tests specific for a variety of physiological and biochemical characteristics. Often, a number of specific colonies must be sequentially tested. In some cases, the overgrown gram negative bacteria (such as the swarming Proteus spp.) on the culture plates prevent accurate identification of specific colonies for subsequent tests. Additionally, the isolated cultures must be confirmed through antibiotic susceptibility tests for vancomycin resistance.

These methods are labor intensive, time consuming, and require highly skilled medical technologists or microbiologists to perform the tests. The above described methods usually take at least 2–3 days to complete, and are suspectible to false positives and false negatives.

The use of chromogenic or fluorogenic enzyme substrates have been widely used in microbial diagnostic methods. For example, Edberg (U.S. Pat. No. 4,925,789) described using a nutrient indicator which not only serves as a nutrient indicator, but also changes color upon being metabolized. This patent, herein incorporated by reference, provides a medium containing a nutrient indicator which, when metabolized by target bacteria, releases a moiety which imparts a color or other detectable change to the medium. The procedure takes advantage of enzyme specificity unique to particular speciies of groups of bacteria. It describes using antibiotics to select for growth of the target microorganisms and provides a specific example of liquid based assay.

Kilian et al. *Acta Path. Microbiol. Scand.* Sec. B 87 271–276 (1979) and Demare et al.,*J. Food Science* 50:1736 (1985) report use of agar-based media without antibiotics. Chen and Gu, U.S. Ser. No. 08/335,149, filed Nov. 4, 1994, incorporated by reference herein, described the use of a fluorogenic nutrient indicator, 4-methylumbelifery-β-D-glucopyranoside, in a microbe-specific medium for detecting Enterococci. Each of the above described methods, however, is not suitable for detecting vancomycin-resistant Enterococci.

The above discussion is not an admission that any of the references discussed is prior art to this invention.

SUMMARY OF THE INVENTION

The present invention provides a method and media for specific detection of target microbes in a clinical sample. One of the problems in clinical sampling is that many bacteria are physiologically or biochemically similar, since these organisms reside in the same ecological system such as gastrointential tract of humans. Therefore, a simple, single enzyme reaction is often insufficient to specifically detect an organism in a medium. To achieve specific detection of target microbes, at least two enzymes should be used.

According to the present invention, a medium is provided in the method of performing a microbial diagnostic test, in which target microbes metabolize at least two nutrient indicators to yield detectable signals, and in which the presence of target microbes is indicated by the detectable characteristics yielded by two specific enzymatic reactions. The specific enzymes include β-glucosidase and pyrrolidonyl arylamidase.

Preferably, the two or more nutrient indicators yield distinctively different detectable signals so that the presence of both or more detectable signals is distinctively detectable from the presence of only one or some of the detectable signals. In such a case, the two or more nutrient indicators can be detected at the same or about the same time. For example, one nutrient indicator gives a color in the visual range while another nutrient indicator produces fluorescence under a ultraviolet lamp.

However, in designing aqueous assay systems using two chromogenic or two fluorogenic compounds as nutrient indicators, it s often difficult or even impossible to find two nutrient indicators with different colored products, or whose signals do not interfere with each other. Obviously, two indicators which yield the same color would be useless for detecting the presence of both. A less obvious problem exists when a strong red colored product masks a light yellow signal, or when a blue colored product quenches a fluorescent signal. To overcome these problems, this invention uses a second nutrient indicator that produces a colorless intermediate product which, upon reacting with a developing agent, generates a second detectable signal, e.g. on a filter paper. This approach prevents interference from the colored product of the first nutrient indicator in the medium. Thus, specific detection of vancomycin-resistant Enterococci in a sample is achieved in this invention by using sequential detection of metabolic hydrolysis of two nutrient indicators in the medium.

Thus, in a first aspect, this invention features a medium for detecting two or more bacterial enzymes. The medium contains a first nutrient indicator for a first bacterial enzyme. The first nutrient indicator provides a first detectable signal when cleaved by the first bacterial enzyme. The medium also contains a second nutrient indicator for a second bacterial enzyme. The second nutrient indicator provides an intermediate molecule when cleaved by said second bacterial enzyme. The intermediate molecule provides a second detectable signal upon reacting with a developing agent.

In preferred embodiments, the first bacterial enzyme is β-glucosidase and the first nutrient indicator may be selected from the group of β-glucosidase substrates consisting of resofuran-β-D-glucopyranoside, o-nitrophenyl-β-D-glucopyranoside, p-nitrophenyl-β-D-glucopyranoside, 5-bromo-4-chloro-3-indoxyl-β-D-glucopyranoside, 6-bromo-2-naphtyl-β-D-glucopyranoside, Rose-β-D-glucopyranoside, VQM-Glc(2-{2-[4-(β-D-glucopyranosyloxy)-3-methoxyl]vinyl)-1-methyl-quinolinium iodide, VBZTM-Gluc(2-{2-[4-(β-D-glucopyranosyloxy)3-methoxylphenyl]vinyl}-3-methylbenzothiazolium iodide, and 4-methylumbelliferyl-β-D-glucopyranoside. This list is not meant to exclude β-glucosidase substrates which have yet to be discovered but may later be identified and included in this list by those of ordinary skill in the art.

In other preferred embodiments, the second enzyme is pyrrolidonyl arylamidase and the intermediate molecule alters the color of said medium upon reacting with a color developing agent. The second nutrient indicator is pyroglutamic acid-β-naphtylamide, and the preferred color developing agent is p-dimethylaminocinnamaldehyde.

By "medium" is meant a solid, semi-solid, powder or liquid mixture which contains all, substantially all, or some of the nutrients necessary to support bacterial growth. Amino acids, minerals, vitamins, and other elements known to those skilled in the art to be necessary for bacterial growth are provided in the medium, which include, but are not limited to, those disclosed in U.S. application Ser. No. 08/335,149, filed on Nov. 4, 1994, incorporated by reference herein. In a preferred embodiment, the medium is liquid. In another preferred embodiment, the medium is agar. In yet another preferred embodiment, the medium is in powder form which upon rehydration allows the growth and detection of bacteria such as vancomycin-resistant Enterococci. The medium of this invention is free of visable target microbes; otherwise, it may be sterile or non-sterile.

For example, the following components are provided in the medium in approximately the amounts indicated. Those in the art will understand that not every component is required. Components may also be substituted with other components of similar properties. The amounts of components may also be varied.

Amino acids may be provided from a variety of sources. These can be provided from natural sources (e.g., extracts of organisms), as mixtures, or in purified form. The natural mixtures may contain varying amounts of such amino acids and vitamins. Not all amino acids must be provided, and the relative amount of each can vary. For general guidance, specific amounts of such amino acids and vitamins are indicated below. These amounts are for guidance only and are not limiting in this invention. Those in the art will recognize that many different combinations of amino acids and vitamins can be used in the medium of this invention. The lists provided below exemplify just one such example. Normally, only amino acids which cannot be synthesized endogenously by the microorganisms to be detected must be provided. However, other amino acids may be provided without departing from the medium of the invention.

The medium preferably includes at least the following amino acids in approximately the following amounts (per liter of medium): alanine (0.1 to 0.3 grams), arginine (0.1 to 0.3 grams), aspartic acid (0.4 to 0.7 grams), cystine (0.01 to 0.015 grams), glutamic acid (1.0 to 1.6 grams), glycine (0.12 to 0.17 grams), histidine (0.116 to 0.17 grams), isoleucine (0.25 to 0.37 grams), leucine (0.4 to 0.6 grams), lysine (0.37 to 0.56 grams), methionine (0.13 to 0.19 grams), phenylalanine (0.2 to 0.3 grams), proline (0. 4 to 0.6 grams), serine (0.18 to 0.26 grams), theronine (0.19 to 0.28 grams), tryptophan (0.05 to 0.07 grams), tyrosine (0.12 to 0.18 grams), and valine (0.29 to 0.44 grams).

Salts may be provided as a source of ions upon dissociation. Such salts may include (per liter of medium): potassium chloride (e.g., about 0.5 to 1.5 grams); copper sulfate (e.g., about 40 to 50 µg); ammonium sulfate (eg., about 4.0 to 6.0 grams); potassium iodide (e.g., about 50.0 to 150.0 µg); manganese sulfate (e.g., about 300.0 to 500.0 µg); sodium molybdate (e.g., about 150.0 to 250.0 µg); zinc sulfate (e.g. about 300.0 to 500.0 µg); and sodium chloride (e.g. about 0.05 to 0.15 g).

Other inorganic moieties may be included to aid microbial growth. These include the following (to the extent not already provided in the above sources of various chemical entities and described in amounts per liter): Phosphorus (about 0.5 mg), Potassium (about 0.4 mg), Sodium (about 30 to 60 mg), and trace amounts of Calcium, Magnesium, Aluminum, Barium, Chloride, Cobalt, Copper, Iron, Lead, Manganese, Suffate, Sulfur, Tin and Zinc.

Vitamins required for growth and reproduction of the microorganism sought to be detected may also be provided. These can be provided in a pure form or as part of a more complex medium. Vitamins may be present in approximately the following amounts (per liter of medium): biotin (about 220 to 330 $\mu$g), pantothenic acid (about 44 to 6 $\mu$g), pyridoxine (about 9 to 14 mg), riboflavin (about 11 to 17 mg), folic acid (about 6 to 8 mg), thiamine (about 16 to 24 mg), niacin (about 15 to 23 mg), and trace amount (less than 10 $\mu$g) of cyanocobalamin.

The medium may also contain an agent which induces enzyme activity. This agent may be an analog to the nutrient indicator. For example, isopropyl-$\beta$-D-thiogalactoside (IPTG) induces $\beta$-galactosidase activity. Ethyl-$\beta$-D-thioglucoside induces $\beta$-glucosidase activity. L-pyroglutamamide, L-pyroglutamic acid, and pyroglutamic acid penta-chloropenyl ester induce pyrrolidonyl arylamidase activity.

By "bacterial enzyme" is meant an enzyme whose enzymatic activity such as the ability to hydrolyse a substrate or a plurality of substrates is characteristic of a bacterium or a plurality of bacteria. In this invention, the enzymatic activities of a bacterial enzyme or bacterial enzymes are used to detect the presence or measure the concentration of bacteria in a test sample. The bacterial enzymes include all those known to one skilled in the art, including, but not limited to, those listed in *Enzymes,* 3rd edition, edited by Malcolm Dixson, Edwin C. Webb, C. J. R. Thorne, and K. F. Tipton, 1979, Academic Press, U.S.A. Examples include, but are not limited to, alkaline phosphatase, acid phosphatase, esterase, lipase, N-acetyl-$\beta$-D-galactosaminidase, N-acetyl-$\beta$-D-glucosaminidase, Neuraminidase, L-arabinopyranosidase, $\beta$-D-fucosidase, $\alpha$-L-fucosidase, $\beta$-L-fucosidase, $\alpha$-D-galactosidase, $\beta$-D-galactosidase, $\alpha$-D-glucosidase, $\beta$-D-glucosidase, $\beta$-D-glucuronidase, pyrrolidonyl arylamidase, $\alpha$-D-mannosidase, pyrophosphatase, sulfatase, $\beta$-D-xylosidase, peptidase, aminopeptidase, trypsin, chymotrypsin, and phosphohydrolase. In a preferred embodiment, the bacterial enzyme is selected from the enterococcus specific enzymes consisting of $\beta$-D-glucosidase, pyrrolidonyl arylamidase, and leucine aminopeptidase.

By "nutrient indicator" is meant a molecule or substance containing a nutrient source attached to or conjugated with a moiety which produces either a detectable signal in a medium or an intermediate molecule which provides a detectable signal in the medium upon reacting with a developing agent. The two or more nutrient indicators are provided in an amount to support the growth of target bacteria. As target bacteria grow from the phase in which nutrients are accumulated for reproduction (lag phase) into the phase in which reproduction occurs at a relatively rapid rate (log phase), nutrition requirements change. Consequently, increasing amounts of nutrient indicators are metabolized and detectable signals or intermediates are produced. Nutrient sources may provide essential vitamins, minerals, trace elements, amino acid ingredients or carbon. The nutrient indicator may provide the primary carbon source to support substantial reproductive growth of target microbes until detectable characteristics are produced. Other nutrient sources may also be provided, so long as adequate selectivity and sensitivity of the medium is maintained. For examule, the nutrient indicator may be the primary source of carbon for the target bacteria. Alternatively, other carbon sources may be present (e.g. amino acids) which might be preferentially used by the target bacteria but the amount provided is such that not to reduce the specificity (and preferably, the sensitivity) of the medium.

The moiety attached to or conjugated with the nutrient source may be a detectable moiety or an intermediate molecule. A "detectable moiety" is a molecule or substance which can either be covalently linked to a nutrient source or exist as a separate entity by itself. The detectable moiety does not cause or produce a detectable signal when it is covalently bonded to a nutrient source. However, when a bacterial enzyme hydrolyses the nutrient indicator, the detectable moiety is released and causes or produces a detectable signal. A detectable moiety may be a chromogen or a fluorogen. Fluorogens fluoresce upon exposure to an excitation light source. Fluorogens include, but are not limited to, 4-methylumbelliferone and 7-amido-4-methylcoumarin moieties. Chromogens produce a color change observable in the visible range. Chromogens include, but are not limited to, o-nitrophenyl and bromo-chloro-indole moieties. O-nitrophenyl moieties produce a yellow color when released from the nutrient moiety. Bromo-chloro-indole moieties become blue when released from the nutrient moiety.

An "intermediate molecule" is a molecule or substance which can either be covalently linked to a nutrient source or exist as a separate entity by itself. Unlike a detectable moiety, an intermediate molecule, when released from the nutrient source, does not by itself immediately provide an easily detectable signal. It does provide a detectable signal, however, upon reacting with a developing agent. An exemplary intermediate molecule is $\beta$-naphtylamide, which does not change the color of the medium when released from the nutrient indicator. However, the released $\beta$-naphtylamide produces a pink to red color when mixed with a developing agent, p-dimethylaminocinnamaledhyde.

By "detectable signal" is meant a characteristic change in a medium or sample that is observable or measurable by a physical, chemical, or biological means known to those skilled in the art. A detectable signal may be a change in emission or absorbance of visible or invisible light or radio waves at a certain wavelength, electrical conductivity, hybridization, enzymatic reaction, emission of gas, or odor. A detectable signal may also be a change in physical state such as between solid, liquid and gas. In preferred embodiments, detectable signals are changes in color or fluorescent emission of the medium.

Nutrient indicators for $\beta$-glucosidase include, but are not limited to, resofuran-$\beta$-D-glucopyranoside, p-nitrophenyl-$\beta$-D-glucopyranoside, 5-bromo-4-chloro-3-indoxyl-$\beta$-D-glucopyranoside, 6-bromo-2-naphtyl-$\beta$-D-glucopyranoside, Rose-$\beta$-D-glucopyranoside, VQM-Glc(2-{2-[4-($\beta$-D-glucopyranosyloxy)-3-methoxyl]vinyl)-1-methyl-quinolinium iodide, VBZTM-Gluc(2-{2-[4-($\beta$-D-glucopyranosyloxy)3-methoxylphenyl]vinyl}-3-methylbenzothiazolium iodide, and 4-methylumbelliferyl-$\beta$-D-glucopyranoside.

Nutrient indicators for pyrrolidonyl arylamidase include, but are not limited to, L-pyroglutamic acid p-nitroanilide, L-pyroglutamic acid 7-amido-4-methyl-coumarin, and pyroglutamic acid $\beta$-naphtylamide.

The invention also features a method of using the above described medium to sequentially detect the presence or absence of two or more bacterial enzymes in a test sample. The medium is inoculated with the test sample and incubated under conditions suitable for bacteria growth for a certain time period (preferably no more than 24 hours, more preferably no more than 18 hrs, even more preferably no more than 10 hours). The first detectable signal is used as an indication of the presence of the first bacterial enzyme in the test sample. The medium is then brought into contact with a developing agent and the second detectable signal is used as an indication of the presence of the second bacterial enzyme in the test sample.

By "inoculating" is meant mixing the environmental, biological or clinical sample with a liquid medium or liquefied solid medium of this invention or bringing the sample into contact with a semi solid medium.

By "test sample" is meant a piece, fraction, aliquot, droplet, portion, fragment, volume, or tidbit taken from a human or an animal test subject, or from soil, water, air or other environmental sources, or any other sources whose bacterial content needs to be determined. Clinical samples are taken from or coming from human sources. Examples include, but are not limited to, rectal and perirectal swabs, wound swabs, stool specimens, urine specimens, and blood. Environmental and biological samples are taken from or coming from a substance capable of supporting one or more life forms including yeast and bacteria. Examples include, but are not limited to, swabs taking from drinking water, food, utensils or equipment surfaces.

By "bacteria" is mean one or more viable bacteria existing or co-existing collectively in a test sample. The term may refer to a single bacterium (e.g., *Escherichia coli*), a genus of bacteria (e.g. *pseudomonads*), a number of related species of bacteria (e.g. *coliforms*), an even larger group of bacteria having a common characteristic (e.g. all gram-negative bacteria), a group of bacteria commonly found in a food product, an animal, or human subject, or an environmental source, or a combination of two or more bacteria mentioned above. The bacteria include those described or referred to in *Bergev's Manual of Systematic Bacteriology*, 1989, Williams and Wilkins, U.S.A., incorporated by reference herein.

The term "Enterococci" includes, but is not limited to, the following species of microorganisms: *Enterococcus avium, E. casseliflavus, E. cerorum, E. columbae, E. dispar, E. durans, E. faecalis, E. faecium, E. gallinarum, E. hirae, E. malodoratus, E. mundtii, E. pseudoavium, E. raffinosus, E. saccharolyticus, E. seriolicida, E. solitarius,* and *E. sulfureus.* This term is not meant to exclude species which have yet to be discovered but may later be identified and included in this genus by those skill in the art.

The term "vancomycin-resistant Enterococci" includes, but is not limited to, the following species of Enterococci which are able to grow in the presence or at least 16 µg/ml vancomycin: *Enterococcus casseliflavus, E. faecalis, E. faecium,* and *E. gallinarum.* Among them, *E. faecalis* and *E. faecium* are the strains of clinical significance comprising more than 95% of clinical isolates. The term is not meant to exclude species which have yet to be discovered but may later be identified and included in this genus and shown to be resistant to vancomycin by those of skill in the art.

By "selective agents" is meant antibiotics which prevent or inhibit the growth of fungi and gram negative bacteria and prevent microbes other than Enterococci from metabolizing the nutrient indicators. Selective agents include, but are not limited to, sodium azide, sodium chloride, thallium acetate, nalidixic acid, enoxacin, cinoxacin, ofloxacin, norfloxacin, gentamicin, neomycin, bile salts, lincomycin, colistin, ansiomycin, and cycloheximide. Preferably, it includes (per liter of medium) amikacin sulfate (e.g. about 0.005 to 0.015 mg), polymyxin B (about 0.002 to 0.015 mg), amphotericin B (about 0.001 to 0.030 mg), bacitracin (about 0.0004 to 0.0015 mg), cefotaxime (about 0.5 to 5 mg), and clindamycin (about 0.002 to 0.010 mg).

This invention features a medium for detecting the presence or absence of vancomycin-resistant Enterococci. Such a medium contains: (a) vancomycin in an amount sufficient to suppress the growth or vancomycin sensitive Enterococci; (b) one or more selective agents in an amount sufficient to suppress the growth of fungi, gram positive and gram negative bacteria other than Enterococci; c) a first nutrient indicator which provides a first detectable signal when cleaved by β-glucosidase; and d) a second nutrient indicator which provides an intermediate molecule when cleaved by pyrrolidonyl arylamidase, wherein the intermediate molecule provides a second detectable signal upon reacting with a developing agent. Alternatively, the d) above is replaced by a second nutrient indicator which provides a second detectable signal when cleaved by pyrrolidonyl arylamidase, wherein the presence of both the first detectable signal and the second detectable signal is distinctively detectable from the presence of only one of the detectable signals.

In a preferred embodiment, the first nutrient indicator is selected from the group consisting of resofuran-β-D-glucopyranoside, o-nitrophenyl-β-D-glucopyranoside, p-nitrophenyl-β-D-glucopyranoside, 5-bromo-4-chloro-3-indoxyl-β-D-glucopyyranoside, 6-bromo-2-naphtyl-β-D-glucopyranoside, Rose-β-D-glucopyranoside, VQM-Glc(2-{2-[4-(β-D-glucopyranosyloxy)-3-methoxyl]vinyl)-1-methyl-quinolinium iodide, VBZTM-Gluc(2-{2-[4-(β-D-glucopyranosyloxy)-3-methoxylphenyl]vinyl}-3-methylbenzothiazolium iodide, and 4-metylumbelliferyl-β-D-glucopyranoside.

In other preferred embodiments, the second nutrient indicator is pyroglutamic acid-β-naphtylamide; the developing agent is p-dimethylaminocinnamaldehyde.

In a further preferred embodiment, the fist nutrient indicator is o-nitrohenyl-β-D-glucopyranoside for enterococcus β-glucosidase; the second nutrient indicator is pyroglutamic acid β-naphtylamide for enterococcus pyrrolidonyl arylamidase; and the developing agent is p-dimethylaminocinnamaldehyde.

In another preferred embodiment, vancomycin is provided in an amount to inhibit the growth of both vancomycin sensitive Enterococci and non-Enterococci gram positive bacteria, e.g. 12 to 25 milligrams per liter or medium.

The invention also features a method of using the above described medium to detect the presence or absence of vancomycin-resistant Enterococci in a test sample. The medium is inoculated with the test sample and incubated under conditions suitable for Enterococci growth for a certain time period (preferably no more than 24 hours, more preferably no more than 18 hrs, even more preferably no more than 10 hours). After the detection of the first detectable signal (which indicates the presence of β-glucosidase in the test sample), the medium is brought into contact with a developing agent and the second detectable signal is used as an indication for the presence of pyrrolidonyl arylamidase in the test sample. The presence of both the first and second detectable signals indicates that the sample contains vancomycin-resistant Enterococci. The testing medium does not have to be kept sterile, but, obviously must be free of viable target microbes, and the test procedure does not have to be performed in a sterile environment.

In a preferred embodiment, the medium is in powder form, which is liquified with sterile water or non-sterile water before a test sample is inoculated with the medium. The incubation may be performed at a variety of temperatures, but preferably carried out between 35° C. and 45° C.

The term "liquified" means substantially in liquid form, though it is also meant to include pulverized or homogenized samples of solid substances having at least a 10% liquid content. This phrase is meant to exclude a gelled medium, such as is found with agar.

In another preferred embodiment, the method uses an agar medium containing the first and second nutrient indicators. After the detection of the first detectable signal (which indicates the presence of β-glucosidase in the test sample), a developing agent is added on top of the agar medium and the second detectable signal is used as an indication for the presence of pyrrolidonyl arylamidase in the test sample. The presence of both the first and second detectable signals indicates that the sample contains vancomycin-resistant Enterococci.

In yet another aspect, the invention features a method for quantifying the number of vancomycin-resistant Enterococci present in a sample by contacting the sample with the liquefied medium described above, placing the sample and medium mixture in containers, incubating the sample and medium mixture, observing the quantity and quality of detectable characteristic signals, and comparing the quantity of detectable characteristic signals with the most probable number (MPN) values. The MPN technique is based on probability statistics and the results from any type of an MPN analysis are directly related to the frequency of occurrence of a series of positive results that are most likely to occur when given numbers of organisms are present in a sample.

In preferred embodiments, the invention used the apparatus described by Croteau et al. in U.S. Ser. No. 08/557,529, hereby incorporated by reference.

Using the media and methods of this invention, a test sample containing only about 1–10 viable vancomycin-resistant Enterococci per ml can display detectable characteristic changes in 24 hour. The amount of oxygen and carbon dioxide in the medium, amount and type of enzyme inducer present, amount and type of selective agents present, amount of nutrients provided in the medium, and the relative health of the bacteria all affect the detection time. The addition of agents such as pyruvate, which may aid recovery of injured organisms, may increase the speed of detection. If large numbers of bacteria are present in the sample, more rapid detection is also possible. In this invention, the medium provided allows detection of 100–1000 cells/ml in less than 18 hours and 1–10 cells/ml of target microbes in less than 24 hours without cross reactivity from $10^7$ cells of non-target microbes, at least 95% of the time.

This invention can be used in detection of vancomycin resistant Enterococci in such settings as hospitals, clinical and veternary laboratories, and nursing homes. Compared to the existing culture methods in detecting vancomycin resistant Enterococci in a sample, the method of this invention takes shorter time and does not require sterile medium preparation or multiple steps of culture isolation, biochemical identification, and antibiotic susceptibility confirmation. Furthermore, this invention does not require highly skilled medical technologists or microbiologists to perform the test. These advantages make this invention ideal for routine microbiological detection of vancomycin-resistant Enterococci.

Other features and advantages of the invention will be apparent from the following description of the preferred embodiments thereof, and from the claims.

DESCRIPTION OF THE PREFERRED EMBODIMENTS

In the following description, reference will be made to various methods known to those skill in the chemical, biological and microbiological arts. Publications and other materials setting forth such known methodologies to which reference is made are incorporated herein by reference in their entireties as though set forth in full.

Detecting Bacteria with Nutrient Indicators

One approach to test the presence of a particular microorganism or a particular group of microorganisms is to take advantage of the metabolic and physiological characteristics of specific microbes. Specific microorganisms derive their nutrients from an array of sources, some of which may be unique to a particular microorganism or group of microorganisms. Many enzymes have been identified as specific to particular groups or species of microorganisms and others will likely be identified in the future.

Edberg, U.S. Pat. No. 4,925,789 described the use of a nutrient indicator which not only serves as a nutrient source, but also changes color upon being metabolized. The patent, herein incorporated by reference, provides a medium containing minimum nutrients for microbial growth and a nutrient indicator which, when metabolized by a target bacteria, releases a moiety which imparts a color or other detectable change to the medium. The procedure takes advantage of enzyme specificity unique to particular species of groups of bacteria. This minimum-nutrient medium resembles yeast nitrogen base in their overall composition. Yeast nitrogen base, a commercial product of Difco (Difco, Detroit, Mich.), includes sodium chloride, a large amount of ammonium sulfate (a good nitrogen source), and amino acids (histidine, methionine, and tryptophan) in the medium formulation. Yeast nitrogen base differs from Edberg's medium ingredients in the amount of potassium phosphate, sodium carbonate, and sodium pyruvate used, as well as in some other minor aspects. The important feature of yeast nitrogen base is the absence of carbon source in the formulation. This feature accounts for the fact that, while yeast nitrogen base has been used in the classification of yeasts particularly on the basis of carbohydrate requirements, it also serves as a good basal medium to support the growth of non-fastidious bacteria. When nutrient indicators are incorporated into a medium like yeast nitrogen base, they become the primary carbon source for the target bacteria. The carbon source derived from nutrient indicators, when hydrolyzed by target microbes specific enzymes, supports substantial reproductive growth of target microbes until detectable characteristics are produced. In addition, because only limited nutrients are present in this yeast nitrogen base like medium, the growth of fastidious bacteria is prevented. Chen and Gu also described a medium comprising of modified yeast nitrogen base (with the exclusion of potassium phosphate and other salts) and a nutrient indicator for specific detection of Enterococci in a sample in U.S. application Ser. No. 08/335,149, filed Nov. 4, 1994.

Several unique enzymes, including β-glucosidase and pyrrolidonyl arylamidase, have been identified in the Enterococcus group of bacteria (Murray, *Clin. Microbiol. Rev.* 3(1):46–65, 1990). These enzymes hydrolyze chromogenic or fluorogenic substrates under appropriate selective environments to produce a colored or fluorescent signal that can be detected either visually or spectrophotometrically (Littel, et. al., *Appl. Environ. Microbiol.* 45:622–627, 1983, Bosley et. al. *J. Clin. Microbiol.* 18:1275–1277, 1983). Nutrient indicators preferably used in detecting Enterococci (including vancomycin-resistant Enterococci) are the chromogenic substrates, ortho-nitrophenyl-β-D-glucopyranoside and pyroglutamic acid β-naphtylamide.

When viable enterococcus bacteria are present in a sample, the nutrient indicators are metabolized. When cleaved from the nutrient indicator, the indicator portion becomes colored in the medium or becomes colored upon the addition of a color developing agent such as p-dimethylaminocinnamaledhyde. The glucose and the L-pyrrolidone carboxylic acid moieties released from the nutrient indicators are then utilized by vancomycin-resistant Enterococci to promote growth.

In addition to Enterococci, other bacteria that possess β-glucosidase activity include the genera of the family of Enterobacteriacae (e.g. *Enterobacter aerogenes, E. cloacae, klebsiella pneumoniae, Serratia marcescens*), and some of the gram positive bacteria (e.g. *Listeria monocytogenes,* Aerococci, Lactococci, Pediococci, Leuconostoc, and Lactobacilli). In addition to Enterococci, other bacteria that possess pyrrolidonyl arylamidase activity include the genera of Staphylococcus, Lactococcus, Aerococcus, and few Lactobacillus. Bacteria that possess both β-glucosidase and pyrrolidonyl arylamidase activities include *Serratia marcescens,* some of the Lactococci and Aerococci as well as a few Lactobacillus.

Vancomycin is an antibiotic primarily used against gram positive bacteria. It inhibits cell wall biosynthesis and thus prevents the growth of sensitive bacteria. Some Enterococci, which in general are susceptible to vancomycin, have emerged resistance to this antibiotic by blocking the access of vancomycin to its site of action. This physiological characteristic allows one to detect vancomycin-resistant bacteria in the presence of most vancomycin sensitive gram positive bacteria.

Several gram positive bacteria including the genera of Leuconostoc, Pediococcus, and some Lactobacillus, however, are intrinsically resistant to vancomycin.

A medium for detecting and confirming the presence of vancomycin-resistant Enterococci may be produced by utilizing a combination of vancomycin resistance, sequential enzyme specificity, and selective environments. Non-target microbes which do not possess both β-glucosidase and pyrrolidonyl arylamidase activity and can not metabolize the nutrient indicators will not exhibit detectable signals. Heterotrophic bacteria or the vancomycin sensitive non-target microbes that possess both β-glucosidase and pyrrolidonyl arylamidase activity are selectively suppressed by the combination of specifically formulated chemical/antibiotic agents and other physical parameters (pH and temperature).

Typical selective agents that can be used in the medium of this invention to prevent the growth of gram negative bacteria that are not susceptible to vancomycin and possess both β-glucosidase and pyrrolidonyl arylamidase activity include: sodium azide, thallium acetate, nalixidix acid, enoxacin, cinoxacin, ofloxacin, norfloxacin, amikacin, cefotaxime, gentamicin, neomycin, polymyxin, colistin, and bile salts.

The combination of vancomycin resistance, sequential enzyme specificity and antibiotic selectivity provides multiple hurdles which prevent the competing non target bacteria from being detected within the test period, e.g. 24 hours or 18 hours.

Components of Bacterial Growth Medium

Media which have proven optimal in this invention for detecting the presence of vancomycin-resistant Enterococci in a sample include (per liter) a biological buffer, HEPES-free acid (e.g. about 5.0 to 7.0 gram) HEPES-sodium salt (e.g. 7.0 to 9.0 gram), sodium bicarbonate (e.g. 1.5 to 2.5 gram), modified yeast nitrogen base (e.g. 4.0 to 6.0 gram); potassium phosphate (e.g. about 0.1 to 2 grams).

In addition, the following components are provided in the medium in approximately the amounts indicated. Those in the art will understand that not every component is required. Components may also be substituted with other components of similar properties. The amounts of components may also be varied.

Specifically, the medium will have (per liter) a total carbon content of about 3.4 to 5.0 grams with a total metabolizable carbon of about 0.025 to 0.25 grams; a total nitrogen content of about 2.75 to 4.12 grams including an amino nitrogen of about 0.26 to 0.39 grams.

Amino acids required for growth of target microorganisms are also provided. Not all amino acids must be provided and the relative amount of each can vary. Those in the art will recognize that natural sources of such amino acids can be used rather than pure sources. Amino acids may be provided from a variety of sources. These can be provided from natural sources (e.g. extract of whole organisms), as mixtures or in purified form. The natural mixtures can contain varying amounts of such amino acids and vitamins (see below). For general guidance, specific amounts of such amino acids and vitamins are indicated below. These amounts are for general guidance only and are not limiting in this invention. Those in the art will recognize that many different combinations of amino acids and vitamins can be used in media of this invention. The list provided below exemplify just one such example. Normally, only those amino acids which cannot be synthesized endogenously by microorganisms to be detected must be provided. However, other amino acids may be provided without departing from the medium of the invention.

The medium preferably includes at least the following amino acids in approximately the following amounts (per liter of medium): alanine (0.1 to 0.3 grams), arginine (0.1 to 0.3 grams), aspartic acid (0.4 to 0.7 grams), cystine (0.01 to 0.015 grams), glutamic acid (1.0 to 1.6 grams), glycine (0.12 to 0.17 grams), histidine (0.116 to 0.17 grams), isoleucine (0.25 to 0.37 grams), leucine (0.4 to 0.6 grams), lysine (0.37 to 0.56 grams), methionine (0.13 to 0.19 grams), phenylalanine (0.2 to 0.3 grams), proline (0.4 to 0.6 grams), serine (0.18 to 0.26 grams), threonine (0.19 to 0.28 grams), tryptophan (0.05 to 0.07 grams), tyrosine (0.12 to 0.18 grams), and valine (0.29 to 0.44 grams).

Salts may be provided as a source of ions upon dissociation. Such salts may include potassium phosphate (e.g., about 0.5 to 1.5 grams); sodium bicarbonate, (e.g. about 1.5 to 2.5 grams); copper sulfate (e.g. about 40 to 50 μg); ammonium sulfate (e.g. about 4.0 to 6.0 grams); potassium iodide (e.g. about 50.0 to 150.0 μg); manganese sulfate (e.g. about 300.0 to 500.0 μg); sodium molybdate (e.g. about 150.0 to 250.0 μg); zinc sulfate (about 300.0 to 500.0 μg); and sodium chloride (0.05 to 0.15 g).

Other inorganic moieties may be included to aid in microbial growth. These include the following (to the extent not already provided in the above sources of various chemical entities and described in amounts per liter): phosphorus (about 0.5 mg), potassium (about 0.4 mg), sodium (about 30 to 60 mg) and trace elements of calcium, magnesium, aluminum, chloride, cobalt, copper, iron, lead, manganese, sulfur, tin, and zinc.

Vitamins required for growth and reproduction of the microorganisms sought to be detected may also be provided.

These can be provided in a pure form or as part of more complex media. Such vitamins may be present in approximately the following amounts (per liter of medium): biotin (about 220 to 330 μg), pantothenic acid (about 44 to 66 μg), pyridoxine (about 9 to 14 mg), riboflavin (about 11 to 17 mg), folic acid (about 6 to 8 mg), thiamine (about 16 to 24 mg), niacin (about 15 to 23 mg), and trace amount (less than 10 μg) of cyanocobalamin.

Those in the art will recognize that carbon, nitrogen, trace elements, vitamins, amino acids and selective agents can be provided in many forms. Generally, it is preferred to have an amount of vitamins and amino acids in the range of the amounts provided above, but those in the art will recognize that the actual properties of each ingredient may be varied so that reduction in the amount of one ingredient can be compensated by an increase in the amount of another. This is particularly relevant when the essential amino acids, trace elements or vitamins of the microbes sought to be detected are known. Some ingredients may be provided in reduced amounts or deleted if they may be synthesized endogenously by the microorganism whose presence is to be determined.

Together, vitamins, amino acids, trace elements, salts and nutrient indicator ingredients allow sufficient growth of the organism so that detectable change of the sample may be observed.

Growth Stimulators $NaHCO_3$ may be incorporated into the medium to create a microaerophilic environments to enhance the recovery of target microbes. Tween-80 and $KH_2PO_4$ stimulate growth of enterococcus species isolated from water (Lachica et al., *J. Appl. Bacteriol.* 31:151–156, 1968). Other trace elements such as specific amino acid(s) (e.g. glutamic acid, L-pyroglutamic acid), and vitamins (lipoic acid) also have growth promoting activities for enterococcus species.

EXAMPLE 1

One medium that has proven optimal for detecting vancomycin-resistant Enterococci is described in Table I.

This medium contains a buffer, 4.635 to 5.665 grams/liter modified yeast nitrogen base, a source or carbon dioxide and phosphors ions, effective amounts of antibiotics to suppress the growth of fungi, gram negative, and gram positive bacteria other than Enterococcci, effective amounts of nutrient indicators including α-nitrophenyl-β-D-glucopyranoside and L-pyroglutamic acid β-naphthylamine, and sufficient amino acids, vitamins, trace elements and minerals to support growth of vancomycin-resistant Enterococci. It was prepared in sterile water.

A 5 milliliter of the medium was dispensed into a test tube aseptically. Each tube of the microbe-specific medium received a 0.1 milliliter inoculum of the decimally diluted microbes under test shown in Table II and III. To assess the sensitivity and selectivity of this medium, the number of bacterial inoculum was estimated according to the standard plating technique using a blood agar medium.

The medium receiving the bacterial inoculum was incubated at 35° C. for 24 hours. The number of vancomycin resistant Enterococci detected by this microbe-specific medium varies with different tested vancomycin resistant Enterococci strains. Its sensitivity is within the range of 100 to 1,000 target microbes/ml in less than 18 hours and 1–10 target microbes/ml in less than 24 hours (Table II) without cross reactivity from at least $10^7$–$10^8$ cells or non-target microbes (Table III).

EXAMPLE 2

66 rectal and perirectal swabs collected from patients suspected to harbor vancomycia resistant Enterococci were tested with the VRE-specific medium described in Example 1. A traditional selective medium, Campylobacter blood agar supplemented with 8 μg clindamycin, was used in comparison to the VRE-specific medium. The specimens were twirled in the liquid and inoculated evenly into both the VRE-specific medium and the reference medium, which were then incubated at 35° C.

17 test samples exhibited detectable signals in the VRE-specific medium within 24 hours for both β-glucosidase (as indicated by the presence of yellow color) and pyrrolidonyl arylamidase (as indicated by the presence of pink of yellow color upon the addition of p-dimethylaminocinnamaldehyde). All 17 positive specimens were confirmed to contain vancomycin-resistant Enterococci. In addition, no vancomycin-resistant Enterococci were isolated from the 49 test samples that did not exhibit detectable signals.

16 reference plates inoculated with test samples had colonies typical of Enterococci. These cultures were isolated and confirmed for the presence of vancomycin-resistant Enterococci through selective isolation, physiological and biochemical identification, and antibiotic susceptibility test. Another reference plate contained swarming bacteria which hindered result interpretation (this bacteria covered the entire plate); vancomycin-resistant Enterococci were isolated from this plate after a number of subculturing.

These results indicated that the detection method using the VRE-specific medium is at least as sensitive and specific as the reference method in detecting vancomycin resistant Enterococci. The confirmation process for the microbe-specific medium described above is not an admission for the requirements of confirmation steps to verify the presence of vancomycin resistance Enterococci. It was performed to demonstrate that the detection method of this invention is specific and sensitive, and does not require confirmation steps.

EXAMPLE 3

A vancomycin-resistant Enterococci specific medium which contains a buffer, 4.635 to 5.665 grams/liter modified yeast nitrogen base, a source of carbon dioxide and phosphorus ions, effective amounts of antibiotics to suppress the growth of fungi, gram negative, and gram positive bacteria other than Enterococci, effective amounts of the chromogenic nutrient indicator, o-nitrophenyl-β-D-glycopyranoside, and the fluorogenic nutrient indicator, L-pyroglutamic acid 7-amido-4-methyl-coumarin, and sufficient amount of amino acids, vitamins, trace elements and minerals to support the growth of vancomycin-resistant Enterococci The medium components for the medium are the same as those described in Table I except that L-pyroglutamic acid 7-amido-4-methyl-coumarin was used as the nutrient indicator instead of L-pyroflutamic acid β-naphtylamine. It was prepared in sterile water.

A 5 milliliter of the medium was dispensed into a test tube ascetically. One tube of the microbe-specific medium (in triplicate) received an inoculum of approximate 50 cfu/ml vancomycin-resistant Enterococci. Other tubes of the microbe-specific medium received approximate $10^7$ cfu of vancomycin-sensitive Enterococci. The medium receiving the bacterial inoculum was incubated at 35° C. for 24 hours. The tubes containing vancomycin-resistant Enterococci exhibits both yellow color (due to the hydrolysis of o-nitrophenyl-β-D-glucopyranoside) and blue fluorescence under a long wave length ultraviolet lamp (due to the hydrolysis of L-pyroglutamic acid 7-amido-4-methyl-coumarin) after 24 hours of incubation at 35° C. The tubes receiving vancomycin-sensitive Enterococci did not produce both yellow color and blue fluorescence incubating at 35° C. for 48 hours.

All publications referenced are incorporated by reference herein, including drawings and sequences listed in each publication. All the compounds disclosed and referred to in the publications mentioned above are incorporated by reference herein, including those compounds disclosed and referred to in articles cited by the publications mentioned above.

Other embodiments of the is invention are disclosed in the following claims.

TABLE I

COMPONENT I INGREDIENT

| | Source | Preferred Amount (grams/iter) | Range (grams/liter) |
|---|---|---|---|
| Nitrogen | Amino Nitrogen | 0.325 | 0.26–0.39 |
| Amino | alanine | 0.2325 | 0.1–0.3 |
| Acids | arginine | 0.23 | 0.3–0.3 |
| | aspartic Acid | 0.585 | 0.4–0.7 |
| | glutamic Acid | 1.3025 | 1.0–1.6 |
| | glycine | 0.145 | 0.116–0.17 |
| | histidine | 0.145 | 0.116–017 |
| | isoleucine | 0.305 | 0.24–0.37 |
| | cystine | 0.01185 | 0.01–0.015 |
| | leucine | 0.505 | 0.4–0.6 |
| | lysine | 0.465 | 0.373–0.56 |
| | methionine | 0.1575 | 0.13–0.19 |
| | phenylalanine | 0.25 | 0.2–0.3 |
| | proline | 0.52 | 0.4–0.6 |
| | serine | 0.22 | 0.18–0.26 |
| | threonine | 0.235 | 0.19–0.28 |
| | tryptophan | 0.06 | 0.048–0.072 |
| | tyrosine | 0.1475 | 0.12–0.18 |
| | valine | 0.365 | 0.29–0.44 |
| Elements | calcium | 0.003 | 0.001–0.02 |
| | chloride | trace | |
| | cobalt | trace | |
| | Iron | trace | |
| | lead | trace | |
| | manganese | trace | |
| | phosphorus | 0.0005 | 0.0001–0.01 |
| | potassium | 0.0004 | 0.0001–0.01 |
| | sodium | 0.05 | 0.03–0.06 |
| Vitamins | biotin | 0.00027 | 0.00022–0.000324 |
| | pantothenic acid | 0.05515 | 0.044–0.066 |
| | folic acid | 0.00702 | 0.006–0.008 |
| | inositol | 0.002025 | 0.001–0.003 |
| | niacin | 0.0189 | 0.015–0.023 |
| | p-aminobenzoic acid | 0.0002 | 0.0001–0.0003 |
| | pyridoxine hydrochloride | 0.0115 | 0.009–0.014 |
| | riboflavin | 0.0142 | 0.011–0.017 |
| | thiamine hydrochloride | 0.01965 | 0.016–0.024 |

TABLE I-continued

COMPONENT II INGREDIENT

| Ingredients | Range Preferred amount (g/liter) |
|---|---|
| (N-[2-Hydroxyethyl]piperazine-N'-[2-ethanesulfonic acid)-free acid | 4.032–4.0928 |
| (N-[2-Hydroxyethyl]piperazine-N'-[2-ethanesulfonic acid)-sodium salt | 7.301–8.933 |
| Modified yeast nitrogen base | 4.635–5.665 |
| Sodium bicarbonate | 1.8–2.2 |
| Potassium phosphate, monobasic | 0.1–1.0 |
| Nutrient Indicators | |
| o-Nitrophenyl-β-D-glucopyranoside | 0.005–0.2 |
| L-pyroglutamic acid β-naphthylamide | 0.005–0.2 |
| Antibiotics | |
| Vancormycin hydrochloride | 0.015–0.025 |
| Clindamycin | 0.002–0.010 |
| Amikacin sulfate | 0.005–0.015 |
| Cefotaxime | 0.0005–0.005 |
| Polymyxin B | 0.001–0.010 |
| Bacitracin | 0.0005–0.0007 |
| Amphotericin B | 0.001–0.003 |

*Trace = less than 0.001 g/liter

TABLE II

Estimate Detection Limit on Vancomycin-Resistant Enterococci Specific Medium

| Vancomycin-resistant enterococci strains | MIC* (μg/ml) | Detection Limit (cells/ml) | | |
|---|---|---|---|---|
| | | 16 hours | 18 hours | 24 hours |
| Enterococcus faecium VRE02 | >256 | 480 | 480 | 0.048 |
| Enterococcus faecium VRE03 | >256 | 5,600 | 560 | 0.56 |
| Enterococcus faecium VRE04 | >256 | 1,000 | 100 | 0.1 |
| Enterococcus faecium VRE05 | >256 | 9,800 | 980 | 9.8 |
| Enterococcus faecium VRE06 | >256 | 1,000 | 100 | 10 |
| Enterococcus faecium VRE07 | >256 | 10,000 | 1,000 | 10 |

*MIC refers to the minimum inhibitory concentration for vancomycin

TABLE III

Selectivity of Vancomycin-Resistant Enterococci Specific Medium Against Non-Target Bacteria

| Strains | Comments | Cell Numbers Suppressed 24 hours at 35° C. |
|---|---|---|
| Escherichia coli ATCC 25922 | gram negative bacteria | >10$^8$ |
| Klebsiella pneumoniae ATCC 31488 | gram negative bacteria | >10$^8$ |

TABLE III-continued

Selectivity of Vancomycin-Resistant Enterococci Specific Medium Against Non-Target Bacteria

| Strains | Comments | Cell Numbers Suppressed 24 hours at 35° C. |
|---|---|---|
| *Enterobacter cloacae* ATCC 13047 | gram negative bacteria | $>10^8$ |
| *Titrobacter freundii* ATCC 8010 | gram negative bacteria | $>10^8$ |
| *Serratia marcescens* ATCC 43862 | gram negative bacteria | $>10^8$ |
| *Pseudomonas aeruginosa* ATCC 16145 | grain negative bacteria | $>10^8$ |
| *Enterococcus faecalis* ATCC 29212 | vancomycin sensitive | $>10^7$ |
| *Enterococcus faecium* ATCC 19434 | vancomycin sensitive | $>10^7$ |

*MIC refers to the minimum inhibitory concentration for vancomycin

What is claimed is:

1. A medium for detecting vancomycin-resistant Enterococci in a sample form a rectal swab, peri-rectal swab, or stool sample comprising:

vancomycin in an amount sufficient to suppress the growth of vancomycin sensitive Enterococci;

a first nutrient indicator which is a substrate for a first bacterial enzyme and provides a first detectable signal when cleaved by the first bacterial enzyme wherein the first nutrient indicator is a substrate for—β-glucosidase;

a second nutrient indicator which is a substrate for a second bacterial enzyme and provides an intermediate molecule when cleaved by the second bacterial enzyme, and the intermediate molecule provides the second detectable signal upon reacting with a developing agent, wherein the second detectable signal is distinct from the first detectable signal wherein the second nutrient indicator is a substrate for pyrrolidonyl arylamidase;

an effective amount of one or more selective agents active to prevent or inhibit the growth of microorganisms other than Enterococci when a sample from a rectal swab, peri-rectal swab, or stool sample is introduced into the medium wherein the one or more selective agents are selected form the group consisting of: amikacin sulfate, polymyxin B, bacitracin, clindamycin, cefotaxime, amphotericin B, sodium azide, thallium acetate, nalixidic acid, enoxacin, cinoxacin, ofloxacin, norfloxacin, cefotaxime, gentamycin, neomycin, polymyxin B, colistin, and bile salts.

2. The medium of claim 1 wherein the first nutrient indicator produces a detectable color after being cleaved by β-glucosidase.

3. The medium of claim 1 wherein the first nutrient indicator is selected from the group consisting of resofuran-β-glucopyranoside, o-nitrophenyl-β-glycopyranoside, p-nitrophenyl-β-D-glycopyranoside, 5-bromo-4chloro-3-indoxyl-β-D-glucopyranoside, 6-bromo-2-naphtyl-β-D-glycopyranoside, Rose-β-D-glycopyranoside, VQM-Glc(2-{2-[4-(β-D-glucopyranosyloxy)3-methoxyl]vinyl)-1-methyl-quinolinium iodide, VBZTM-Gluc(2-{2-[4-(β-D-glucopyranosyloxy)3-methoxylphenyl]vinyl}-3-methylbenzothiazolium iodide, and 4-methylumbelliferyl-β-D-glycopyranoside.

4. The medium of claim 1 wherein the second nutrient indicator is selected from the group consisting of L-pyroglutamic acid p-nitroanilide, L-pyroglutamic acid 7-amido-4-methyl-coumarin, and pyroglutamic acid β-naphtylamide.

5. The medium of claim 1 wherein the intermediate molecule alters the color of the medium upon reacting with a color developing agent.

6. The medium of claim 5 wherein the second nutrient indicator is pyroglutamic acid-β-naphtylamide.

7. The medium of claim 6 wherein the developing agent is p-dimethylamino-cinnamaldehyde.

8. The medium of claim 2 wherein the first nutrient indicator is o-nitrophenyl-β-D-glucopyranoside.

9. The medium of claim 1 further comprising one or more inducers of enzyme activity for β-D-glucopyranoside.

10. The medium of claim 1 in a liquid form or a gel form.

11. The medium of claim 9 wherein the one or more inducers of enzyme activity are selected form the group consisting of: isopropyl-β-D-thiogalactoside (IPTG), ethyl-β-D-thioglucoside, L-pyroglutamamide, L-pyroglutamic acid, and pyroglutamic acid pentachlorophenyl ester.

12. The medium of claim 1 wherein the first nutrient indicator produces a color in the visual range when cleaved by an enzyme, and the second nutrient indicator produces a fluorescent molecule when cleaved by an enzyme.

13. The medium of claim 12 wherein the medium further comprises a sample from a wound swab, a urine specimen, or a swab from a utensil or equipment surface.

* * * * *

UNITED STATES PATENT AND TRADEMARK OFFICE
CERTIFICATE OF CORRECTION

PATENT NO. : 6,355,449 B1
DATED : March 12, 2002
INVENTOR(S) : Chen et al.

It is certified that error appears in the above-identified patent and that said Letters Patent is hereby corrected as shown below:

<u>Title page,</u>
Item [76], Inventors: delete "Chung-Ming Chen" and replace with
-- Chun-Ming Chen --

<u>Column 17,</u>
Line 18, delete "form" and replace with -- from --.

Signed and Sealed this

Sixteenth Day of July, 2002

Attest:

JAMES E. ROGAN
Attesting Officer   Director of the United States Patent and Trademark Office